United States Patent
McCullough

(10) Patent No.: US 7,827,044 B2
(45) Date of Patent: Nov. 2, 2010

(54) ANALYTICAL TOOL FOR MANAGING THE TREATMENT OF CHRONIC ILLNESSES

(76) Inventor: Thomas J. McCullough, 6446 N. Elm Tree Rd., Milwaukee, WI (US) 53217

( * ) Notice: Subject to any disclaimer, the term of this patent is extended or adjusted under 35 U.S.C. 154(b) by 570 days.

(21) Appl. No.: 11/934,624

(22) Filed: Nov. 2, 2007

(65) Prior Publication Data

US 2009/0119125 A1    May 7, 2009

(51) Int. Cl.
*G06Q 10/00* (2006.01)
(52) U.S. Cl. ................ 705/3; 705/2; 600/300; 600/301
(58) Field of Classification Search ............... 705/2–4, 705/7–8; 600/300–301
See application file for complete search history.

(56) References Cited

U.S. PATENT DOCUMENTS

| | | | |
|---|---|---|---|
| 4,368,509 A | 1/1983 | Li | |
| 5,786,816 A | 7/1998 | Macrae et al. | |
| 5,827,180 A * | 10/1998 | Goodman | 600/300 |
| 5,833,599 A | 11/1998 | Schrier et al. | |
| 6,037,940 A | 3/2000 | Schroeder et al. | |
| 6,315,719 B1 | 11/2001 | Rode et al. | |
| 6,317,719 B1 | 11/2001 | Schrier et al. | |
| 6,684,276 B2 | 1/2004 | Walker et al. | |
| 6,807,531 B1 | 10/2004 | Kanai | |
| 6,980,858 B2 * | 12/2005 | Fuimaono et al. | 607/5 |
| 7,072,840 B1 | 7/2006 | Mayaud | |
| 7,216,084 B2 | 5/2007 | Brinkman et al. | |
| 2002/0128864 A1 | 9/2002 | Maus et al. | |
| 2003/0036683 A1 | 2/2003 | Kehr et al. | |
| 2003/0171657 A1 | 9/2003 | Leonard et al. | |
| 2005/0043965 A1 * | 2/2005 | Heller et al. | 705/2 |
| 2007/0143135 A1 | 6/2007 | Lindquist et al. | |
| 2007/0192146 A1 * | 8/2007 | Menocal et al. | 705/4 |
| 2008/0140445 A1 * | 6/2008 | Wang | 705/2 |
| 2008/0270175 A1 * | 10/2008 | Rodriguez et al. | 705/2 |

FOREIGN PATENT DOCUMENTS

WO    WO9715022    4/1997

* cited by examiner

*Primary Examiner*—Vivek D Koppikar
(74) *Attorney, Agent, or Firm*—Absolute Technology Law Group LLC

(57) ABSTRACT

A system and method for creating an individual treatment plan which includes a user interface configured to receive user input and communicate with a Relational Remedy Database Server containing information about chronic illnesses and remedies. The Method and System described herein further utilizes a Treatment Plan Software Component, a Patient Data Update Software Component and an Optimization Software Component which performs a multiple regression analysis to determine an optimal combination of remedies based on user responses to create an Updated Treatment Plan.

21 Claims, 15 Drawing Sheets

ANALYTICAL TOOL FOR MANAGING THE TREATMENT OF CHRONIC ILLNESSES

FIELD OF INVENTION

The invention relates to the field of treating and managing chronic illnesses and more specifically a system and method to enable users to create an Individual Treatment Plan using a method for optimizing treatment options.

BACKGROUND

Figure 1:
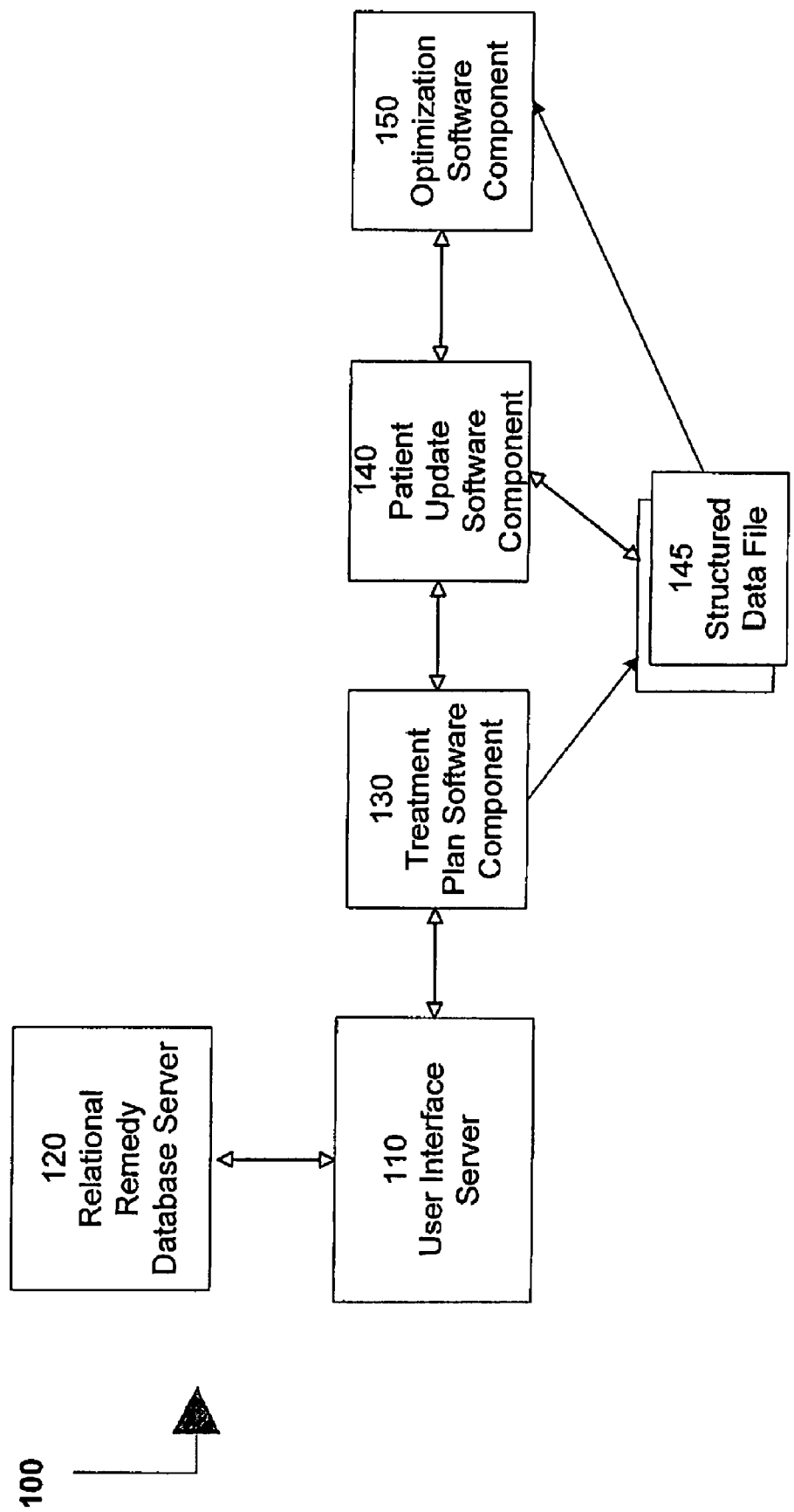
FIG. 1 is a diagram of a system for creating an Individual Treatment Plan which optimizes treatment options.

For the purpose of promoting an understanding of the present invention, references are made in the text hereof to embodiments only some of which are depicted in the figures. It should nevertheless be understood that no limitations on the scope of the invention are thereby intended. One of ordinary skill in the art will readily appreciate that modifications such as the order of steps, or equivalent software or hardware components, or a different distribution of components, positioning of the components relative to one another, and the inclusion of additional elements are deemed readily apparent and obvious to one of ordinary skill in the art, and all equivalent relationships to those illustrated in the drawings and described in the written description do not depart from the spirit and scope of the present invention. Some of these possible modifications are mentioned in the following description. Therefore, specific details disclosed herein are not to be interpreted as limiting, but rather as a basis for the claims and as a representative basis for teaching one of ordinary skill in the art to employ the present invention in virtually any appropriate system or process.

It should be understood that the drawings do not necessarily illustrate the sequence of steps in which the invention may be carried out, and that each step represents a stage of an equivalent processes.

DEFINITIONS

Moreover, the term "approximately" or "substantially" as used herein may be applied to modify any quantitative representation that could permissibly vary without resulting in a change in the basic function to which it is related.

As used herein, the term "chronic illness" refers to any illness having symptoms which may reocur, occur over a period of time or which may manifest itself with different symptoms.

As used herein, the term "design of treatments process" refers to an experimental design of treatment options including but not limited to fractional factorial design, D-optimal design, mixture designs.

As used herein, the term "fractional factorial design" refers to an experimental design comprising a subset of options selected to correspond to the most statistically likely options to create information useful in formulation and individual medical treatment plan. For example, a $2^{5-2}$ design is a two-level, five-factor, ¼ fractional factorial design. Rather than the 32 runs that would be required for the full $2^5$ factorial experiment, this experiment requires only eight runs. Assuming the higher order interaction terms are negligible, the amount of information that is generated from a fractional factorial experiment is comparable to a full factorial experiment, but the practical cost in time, money, or resources is significantly smaller. The levels of a factor are commonly coded as +1 for the high level, and −1 for the low level. For a three-level factor, the intermediate value is coded as a 0.

As used herein, the term "Healthcare Professional" means a provider of medical or therapeutic services, or counseling, consultative or support services related to a chronic illness, whether or not licensed or certified in any capacity, whether or not recognized by the medical community, and whether or not covered by insurance. Healthcare Professionals include but are not limited to physicians, nurses, therapists, chiropractors, consultants and providers of non-traditional health care services.

As used herein, the term "Health Care Professional Communication Software Component" means a software component that enables a Health Care Professional to communicate with a user of the system and method described herein, or to receive communication about the user. Fix and renumber As used herein, the term "Individual Treatment Plan" means a medical treatment plan based upon a combination of remedies selected by a user.

As used herein, the term "input" refers to software, a user interface, an electronic recording device, a manual recording device (such as pen and paper) or combinations thereof for receiving and recording data As used herein, the term "List Generating Software Component" means a software component capable of creating a list of patients based on any criteria tracked by the system and method described herein.

As used herein, the term "menu-selected" means selected from a menu on a user interface.

As used herein, the term "messages" refers to any prompt, communication or data entered into the system described herein, or generated by the system including, but not limited to advertising messages, prompts or data input by a system user.

As used herein, the term "optimization report" refers to a report summarizing treatment options to be utilized pursuant to a design of treatments process taking into account relevant criteria. Criteria may include but is not limited to efficacy of treatment, cost, patient response, physician response, prior statistical success, availability, minimization of side effects, graphs and contour plots, or any other known information or criteria which may be considered in formulating a treatment plan for a chronic illness.

As used herein, the term "patient" means any user of the system and method herein whether or not the user has an affiliation or is under the care of a Health Care Professional.

As used herein, the term "negative interactions" means any undesirable result caused by a combination of remedies, or by at least one remedy and at least one chronic condition.

As used herein, the term "Optimization Software Component" is a software component that utilizes a mathematical multi-variable regression analysis.

As used herein, the term "optimal subsequent combination of remedies" means a combination of remedies modified based on any patient response, response data or information about the patient.

As used herein, the term "Patient Data Update Software Component" means software configured to update known patient data and selections.

As used herein, the term "patient-related list" means any list of patient-related information the system and method described herein are configured to track, including but not limited to how often remedies are selected, data as to success or response to remedies, personal or geographical software about users and symptoms reported.

As used herein, the term "Payment Receiving Software Component" means software configured to receive a form of payment.

As used herein, the term "remedy" or "remedies" means any product, action, therapy, or medicine used to treat an illness, whether or not prescribed or regulated.

As used herein, the term "Relational Remedy Database Server" means a server containing a database which matches known or appropriate remedies to chronic illnesses specified by a user of the system described herein, which is configured to communicate with a user interface as defined herein.

As used herein, the term "Report Generation Software Component" means software configured to create reports in any format using data tracked by the system and method described herein.

As used herein, the term "response" means any form of user feedback or data collected from a user relating to the effectiveness, perceived effectiveness or desirability of a remedy. Responses include any subjective, qualitative, quantitative or numerically valued or scaled responses, such which may potentially be converted to a quantitative value to be used for a regression analysis.

As used herein, the term "structured data file" means any file containing data about a user in any file format or structure.

As used herein, the term "Targeted Advertising Information" means any message or information generated or displayed in response to a specific user input.

As used herein, the term "Targeted Advertising Software Component" means software configured to display any message or information generated or displayed in response to a specific user input.

As used herein, the term "supplier information" means any information relative to a supplier of goods and services related to a treatment option, including location, identification, background, ratings or Targeted Advertising Messages.

As used herein, the term "supplier resource" refers to any supplier of goods or services related to a remedy.

As used herein, the term "treatment option" refers to any non-prescription remedy, prescription remedy, and therapy therapeutic activity, abstinence from an activity or any levels of or combination thereof.

As used herein, the term "Treatment Plan Software Component" means software configured to create an Individual Treatment Plan or to update a treatment plan based on user response or any other user input. The Treatment Plan Software Component generally uses a fractional factorial design or design of treatment process but may use other methods for designating a subset of remedies to be used in creating and successively updating Individual Treatment Plans.

As used herein, the term "updated treatment plan" means a treatment plan that has been modified in accordance with a response.

As used herein, the term "updated user interface" means a user interface that is been modified in accordance with a response or with any other user input.

As used herein, the term "updated user-selected remedies" means a list of user remedies that has been created or modified based on a user response.

As used herein, the term "user interface" includes all software and hardware necessary to display information to a user, receive input from a user and transmit data to and from a server which houses a database or other processing software.

DETAILED DESCRIPTION OF EMBODIMENTS
OF THE INVENTION

FIG. 1 is a flow a flowchart of System 100 for creating an Individual Treatment Plan which includes user interface 110 configured to communicate with Relational Remedy Database Server 120. The user interface may reside on a single server, multiple servers or a network. User interface 110 includes software and hardware configured to receive user input, display a user interface (e.g. a treatment plan) and to transmit and receive data to create an updated user interface.

In the embodiment shown, Relational Remedy Database Server includes data about known remedies for chronic illnesses, and is configured to match known or appropriate remedies to a chronic illness specified by the user from a menu displayed on user interface 110. In the embodiment shown, Relational Remedy Database Server 120 is stored on a single server, but in other embodiments, may be stored on multiple distributed servers or on a network. Relational Remedy Database Server 120 includes software and hardware components necessary for it to communicate with user interface 110 in order to display a list of remedies for one or more chronic illnesses selected corresponding to chronic illnesses selected by the user on user interface 110. In other embodiments, Relational Remedy Database Server 120 may further be configured to identify known remedy interactions and/or allergic reactions, or may be modified to include parameters and other restrictive information entered by Health Care Professionals and system administrators having appropriate permissions to modify or update Relational Remedy Database Server 120.

In the embodiment shown, Relational Remedy Database Server 120 includes data about known remedies for epilepsy, diabetes, cancer, schizophrenia, Alzheimer's, multiple sclerosis, emphysema, allergies, acne, asthma, depression and other psychiatric illnesses, Arthritis, Asthma, Back Pain, Bipolar Disorder, Cancer, Cholesterol, Depression, Cold and Flu, Diabetes, Erectile Dysfunction, Gout, Heart Attack, Heart Disease, Heartburn/GERD, Hemorrhoids, Hernia, Kidney Stones, Migraines and headaches, muscle aches, cancer, shingles, rosacea, allergies, Amyotrophic Lateral Sclerosis. In other embodiments, Relational Remedy Database Server 120 may include more, less, fewer or different remedies and chronic illnesses.

The embodiment shown further includes Treatment Plan Software Component 130 which is software and hardware configured to communicate with user interface 110 to display an Individual Treatment Plan based on remedies selected by a user, as accessed from Relational Remedy Database Server 120. Patient Update Software Component 140 creates a structured data file 145 unique to a user which contains information about the user (e.g., a patient) and any Individual Treatment Plan created.

In the embodiment shown, user interface 110 receives response input from a user relating to the effects of a treatment option or combination of treatment options.

Optimization Software Component 150 which updates the Individual Treatment Plan to include a revised combination of remedies based on user responses as to the effectiveness of the initial remedies selected by the user. In the embodiment shown, Optimization Software Component 150 performs a multiple regression analysis to determine an optimal combination of updated remedies and their levels, and includes these remedies in an Updated Treatment Plan displayed on user interface 110. In the embodiment shown, a structured data file containing the Updated Individual Treatment Plan is transmitted to Patient Data Update Software Component 140, and is used to create an updated user interface. The user may subsequently, after the Updated Treatment Plan is created, enter additional responses and remedy selections to successively update and optimize remedies to create further Updated Treatment Plans, repeating the process as desired by the user. In the embodiment shown, Optimization Software Component 150 may be invoked repeatedly to process additional user responses and remedy selections to create successive Updated Treatment Plans.

In the embodiment shown Optimization Software Component further optimizes treatment options taking into account the cost of treatment options. In the embodiment shown, cost is treated as a dependent variable in optimizing treatment options, and creates cost-optimized treatment plan. The cost of treatment is used to analyze n sets of data to determine the functional relationship among user (e.g. patient) response and cost. Other embodiments may not include cost optimization features or may include more, fewer or different independent variable in the optimization process.

Figure 2:
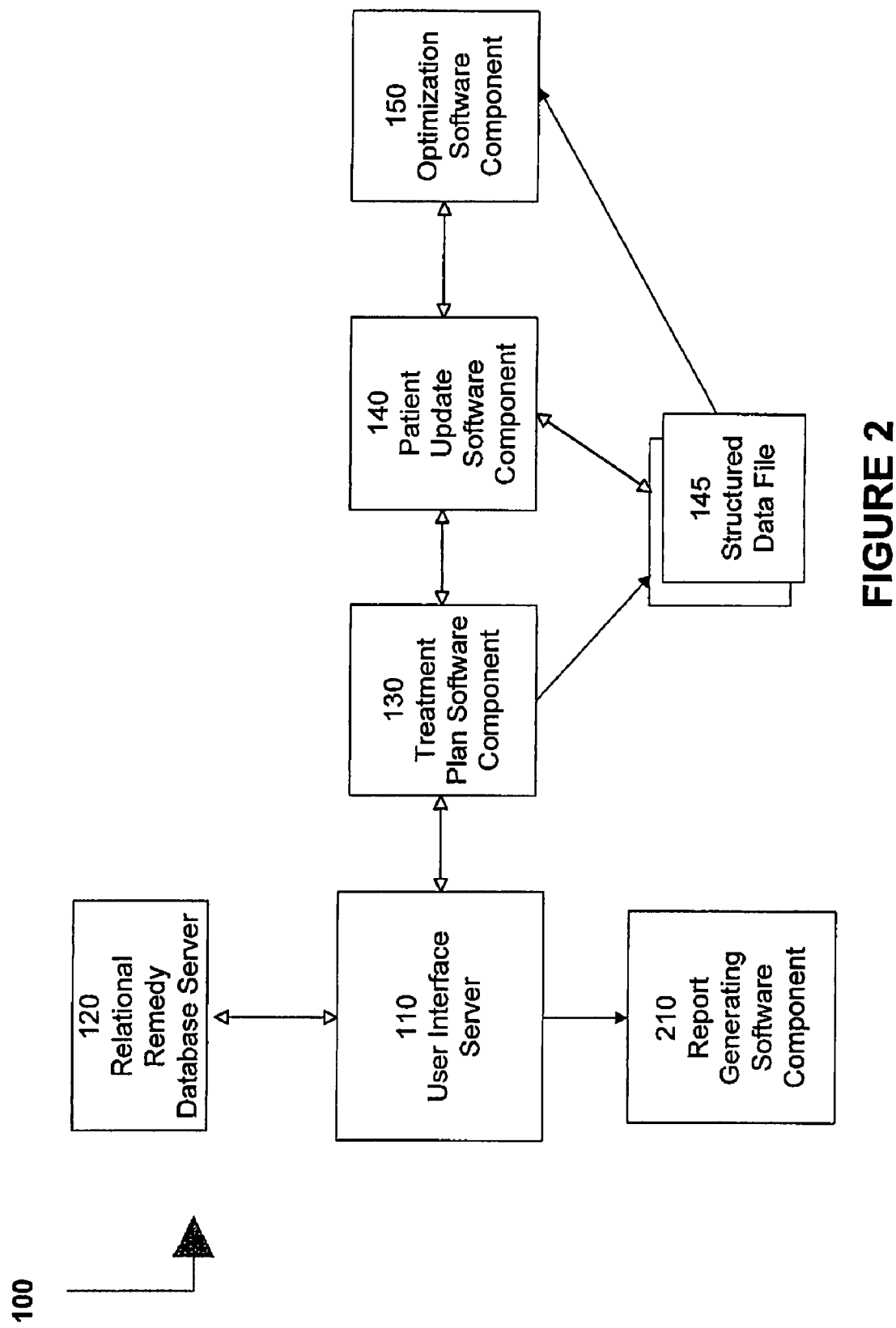
FIG. 2 is a diagram of a system for creating an Individual Treatment Plan which is further configured to generate reports.

FIG. 2 depicts an embodiment of System 100 configured to generate reports, using Report Generating Software Component 210. Reports may be generated as to positive and negative responses, remedy interactions, patient progress, demographic data or any other data which the system is capable of tracking.

Figure 3:
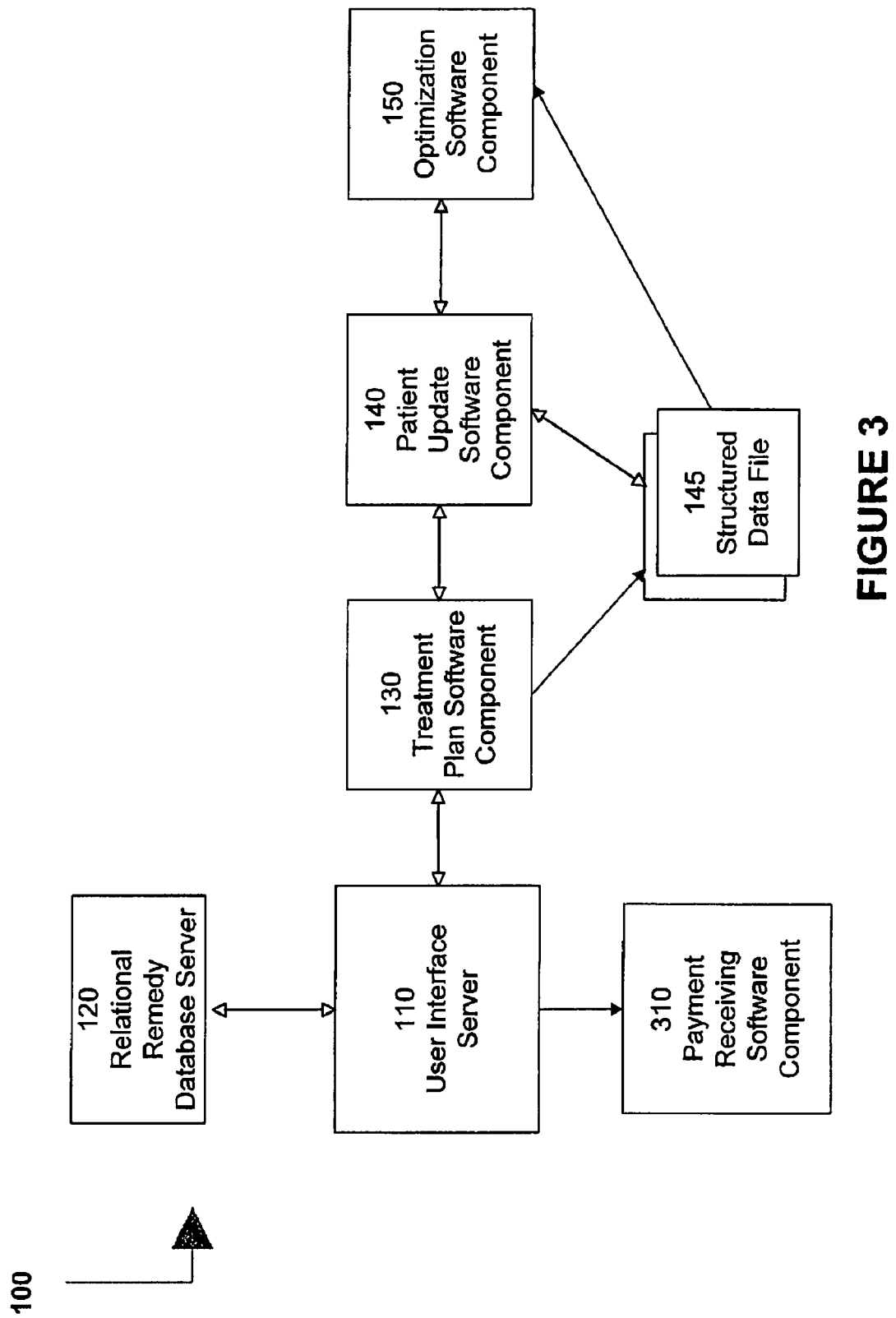
FIG. 3 is a diagram of a system for creating an Individual Treatment Plan which is further configured to receive payments.

FIG. 3 depicts an embodiment of System 100 configured to receive payments from using Payment Receiving Software Component 310. In the embodiment shown, a payment is required in order to save an Individual Treatment Plan for retrieval after in the future, but other embodiments may require no payment or may require payment at different or additional stages.

Figure 4:
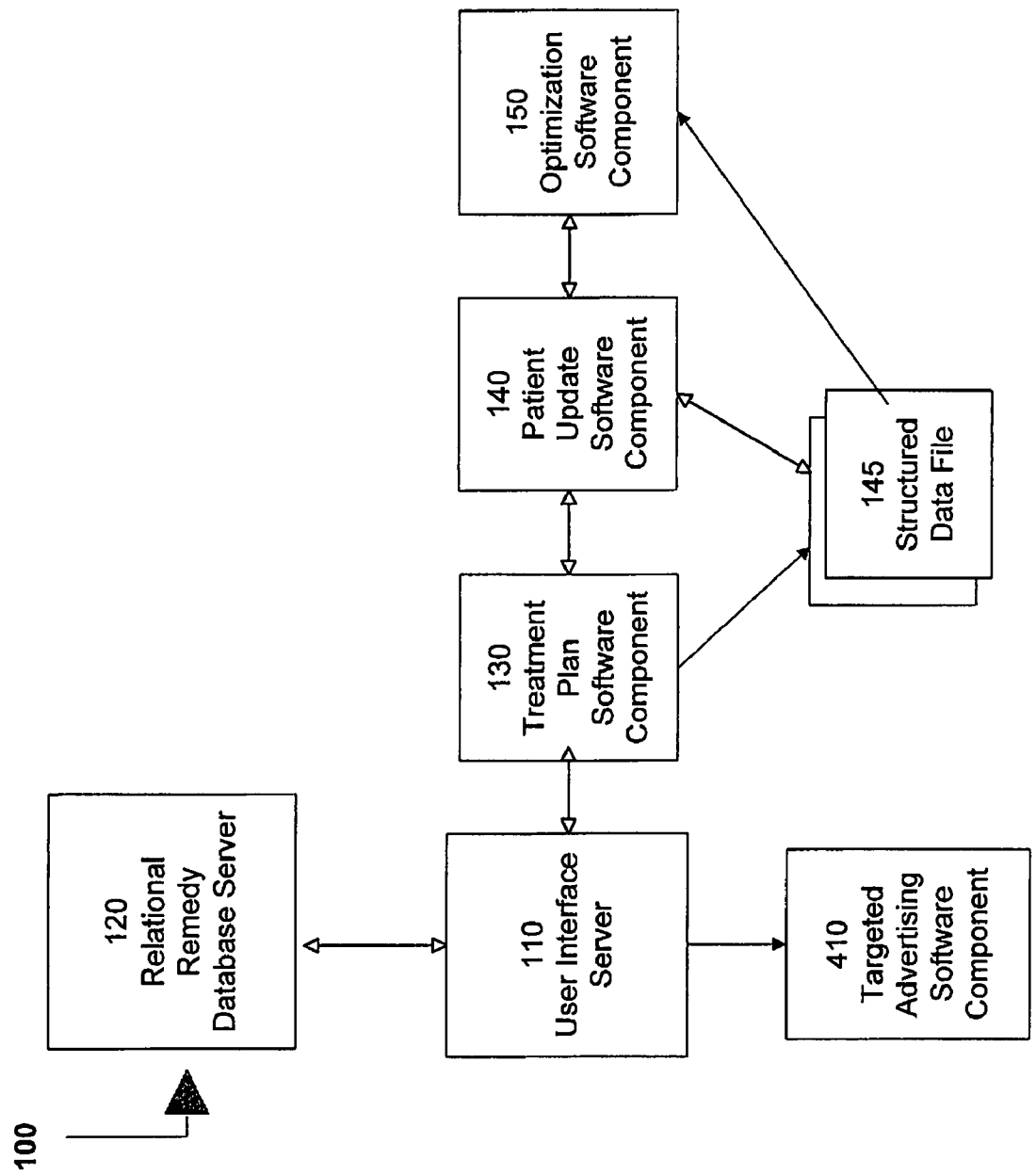
FIG. 4 is a diagram of a system for creating an Individual Treatment Plan which is further configured to create Targeted Advertising Messages.

FIG. 4 depicts an embodiment of System 100 configured to create Targeted Advertising Messages using Targeted Advertising Software Component 410. For example, in one embodiment, a user may input a specific chronic illness and receive one or more messages about new remedies, Health Care Professionals, support groups for persons suffering from that specific chronic illness or other targeted messages.

Figure 5:
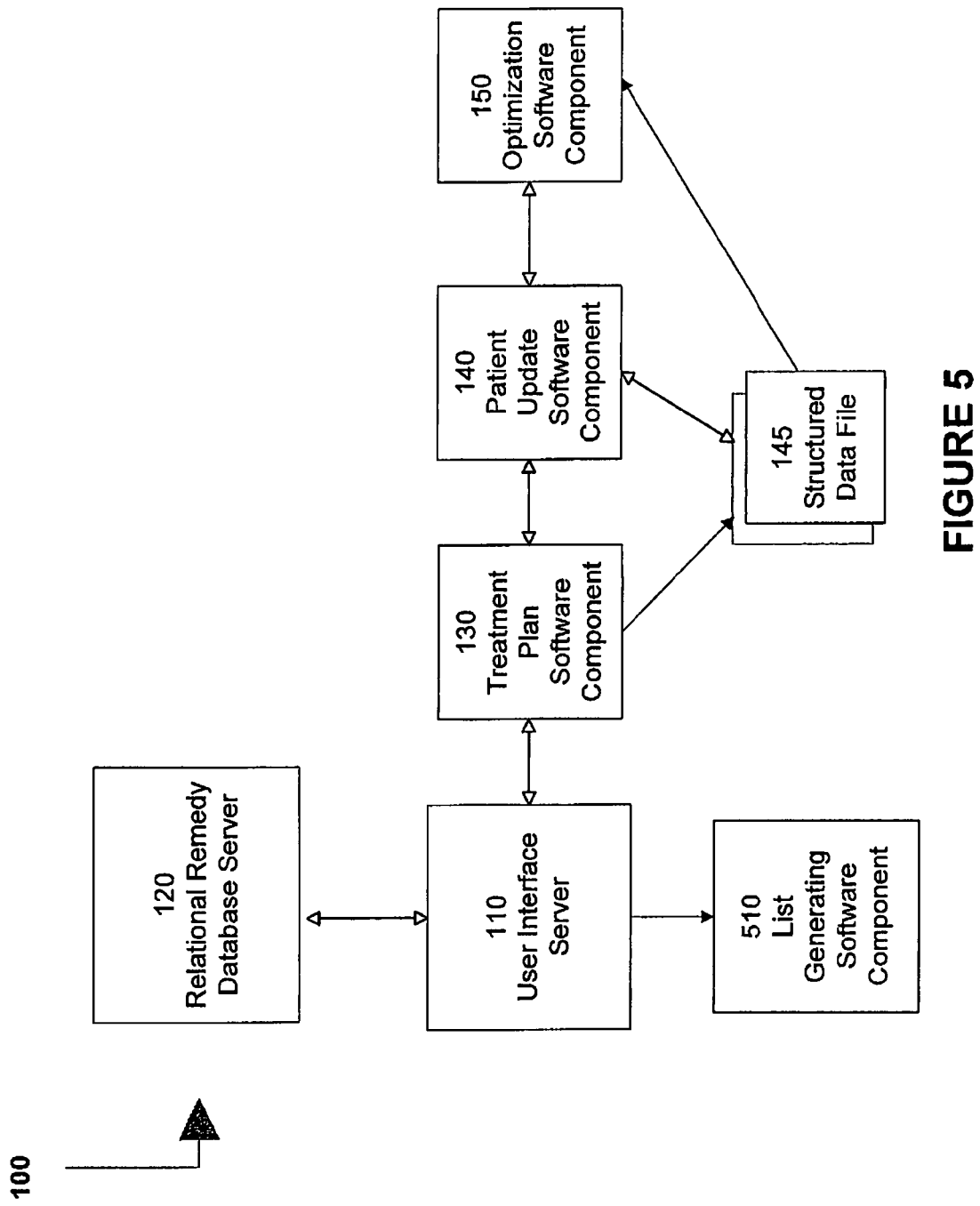
FIG. 5 is a diagram of a system for creating an Individual Treatment Plan which is further configured to generate patient-related lists.

FIG. 5 depicts an embodiment of System 100 configured to create patient-related lists based on data or tracked by the system using List Generating Software Component 510 which may create patient-related lists from demographic data, geographical data, personal profile data, user responses, symptoms or any other data which the system described herein may be configured to track.

Figure 6:
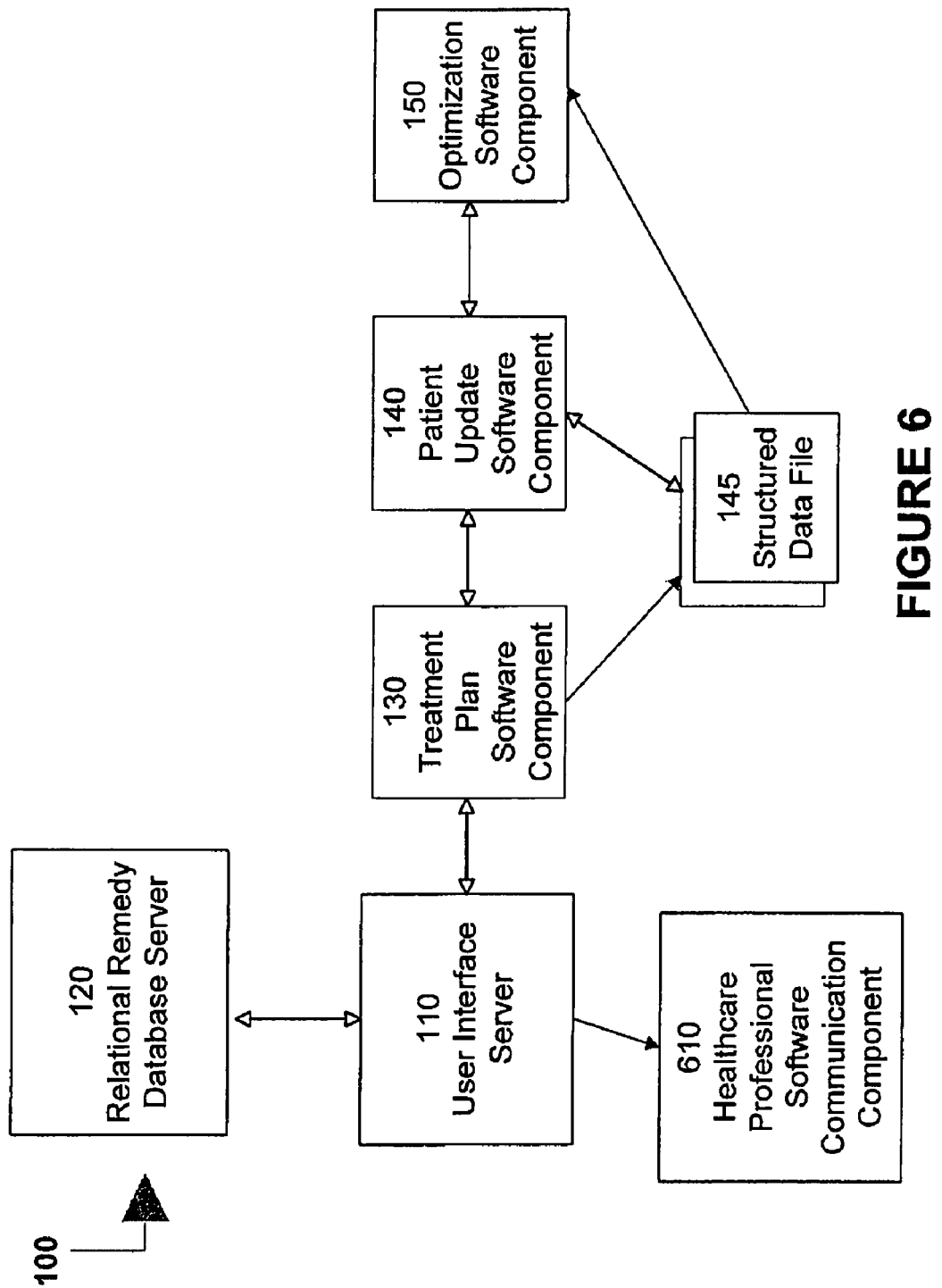
FIG. 6 is a diagram of a system for creating an Individual Treatment Plan which is further configured to enable Health Care Professionals having appropriate permissions to communicate with users.

FIG. 6 depicts an embodiment of System 100 which further includes a Health Care Professional Software Component 610 configured to enable Health Care Professionals having appropriate permissions to communicate with users. One exemplary embodiment of the system is a system used by an oncologist to communicate and develop Individual Treatment Plans for cancer patients.

Figure 7:
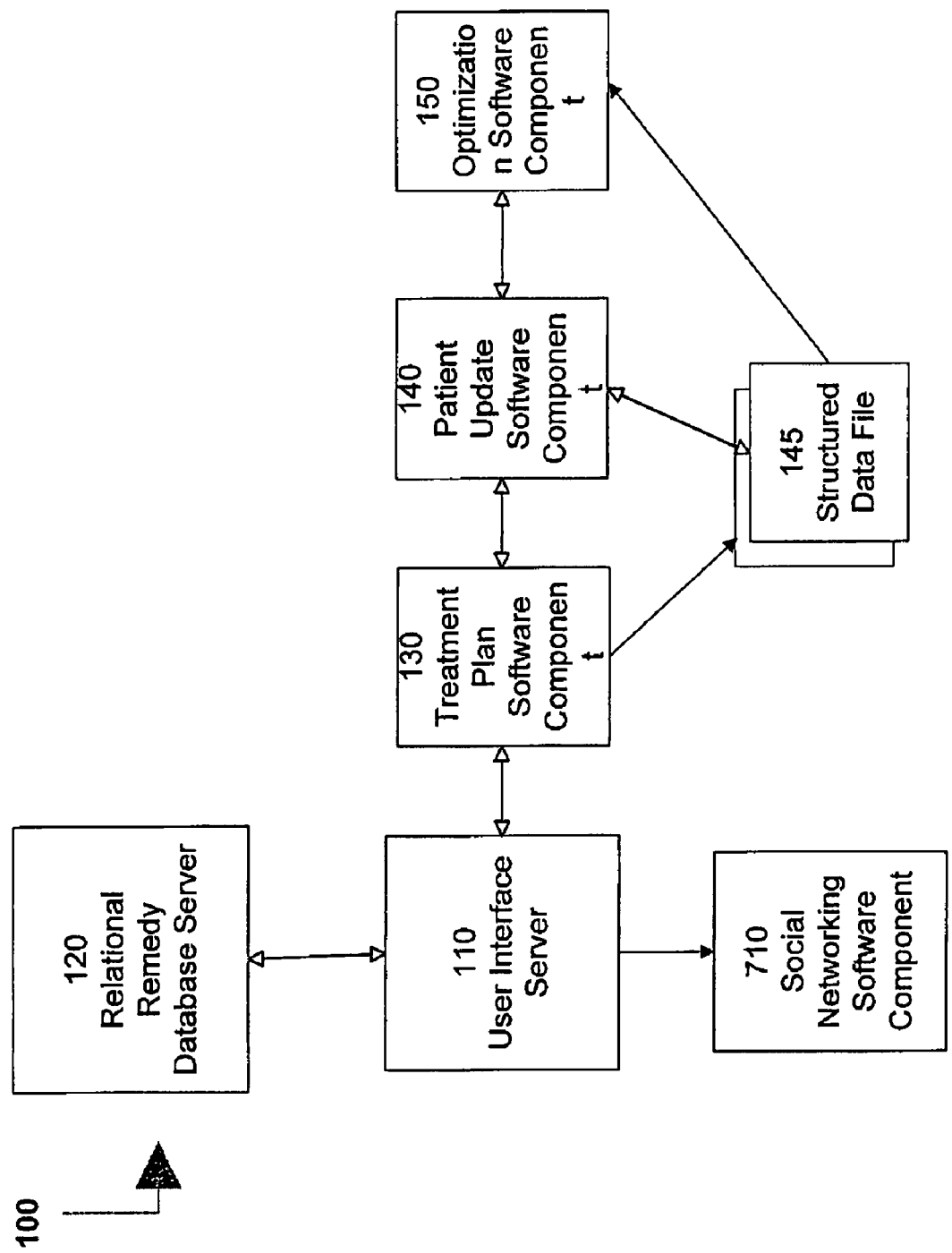
FIG. 7 is a diagram of a system for creating an Individual Treatment Plan which is further configured to enable users to communicate with each other.

FIG. 7 depicts an embodiment of system 100 which further includes Social Networking Software Component 710 configured to enable Health Care Professionals having appropriate permissions to communicate with users.

Figure 8:
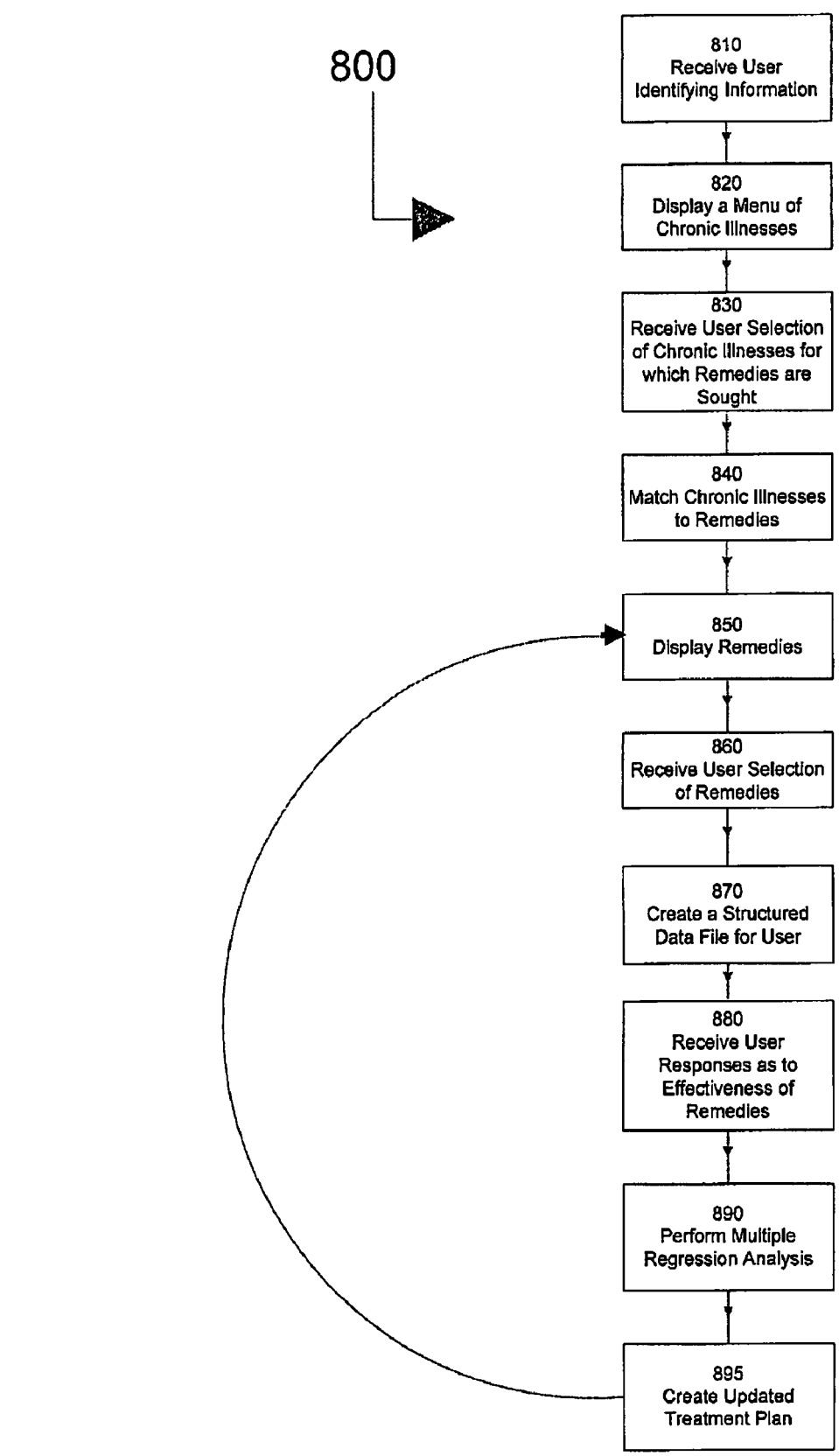
FIG. 8 is a flowchart of a method for creating an Individual Treatment Plan which optimizes treatment options.

FIG. 8 is a flow chart of a Method 800 for creating an Individual Treatment Plan. Step 810 includes receiving identifying information from a user. Identifying information may include the user's name, login, password and/or other personal or health-related information.

Step 820 includes displaying a menu of chronic illnesses on a user interface. In the embodiment shown the user may select one or more chronic illnesses, but other embodiments may limit the user to selecting a single chronic illness or a particular combination of chronic illnesses.

Step 830 includes receiving a user selection of one or more chronic illnesses selected from the menu of chronic illnesses. In Step 840, the chronic illnesses are matched to a relational database which contains known remedies for the chronic illnesses selected. In the embodiment shown, examples of chronic illnesses for which remedies are included in the relational database are includes known remedies for epilepsy, diabetes, cancer, schizophrenia, Alzheimer's, multiple sclerosis, emphysema, allergies, acne, asthma, depression and other psychiatric illnesses, Arthritis, Asthma, Back Pain, Bipolar Disorder, Cancer, Cholesterol, Depression, Cold and Flu, Diabetes, Erectile Dysfunction, Gout, Heart Attack, Heart Disease, Heartburn/GERD, Hemorrhoids, Hernia, Kidney Stones, Migraines and headaches, muscle aches, cancer, shingles, rosacea, allergies, Amyotrophic Lateral Sclerosis. Other embodiments may include more, less, fewer or different chronic illnesses.

Method 800 further includes Step 850 which displays known or appropriate remedies retrieved from a Relational Remedy Database Server for chronic illnesses selected by a user. Step 860 includes receiving user input in which the user selects remedies they wish to consider or try. Step 870 includes creating a structured data file to track user identity, chronic illnesses and remedies selected based on Design of Treatment Process or a Design of Experiment software component. Step 880 includes receiving user response data as to the effectiveness of remedies selected. These responses indicate how effective a user perceives various remedies, and the effectiveness of the remedies as an independent variable. Step 890 utilizes response data to perform a multiple regression analysis, which is used in Step 895 to create an updated treatment plan.

Figure 9:
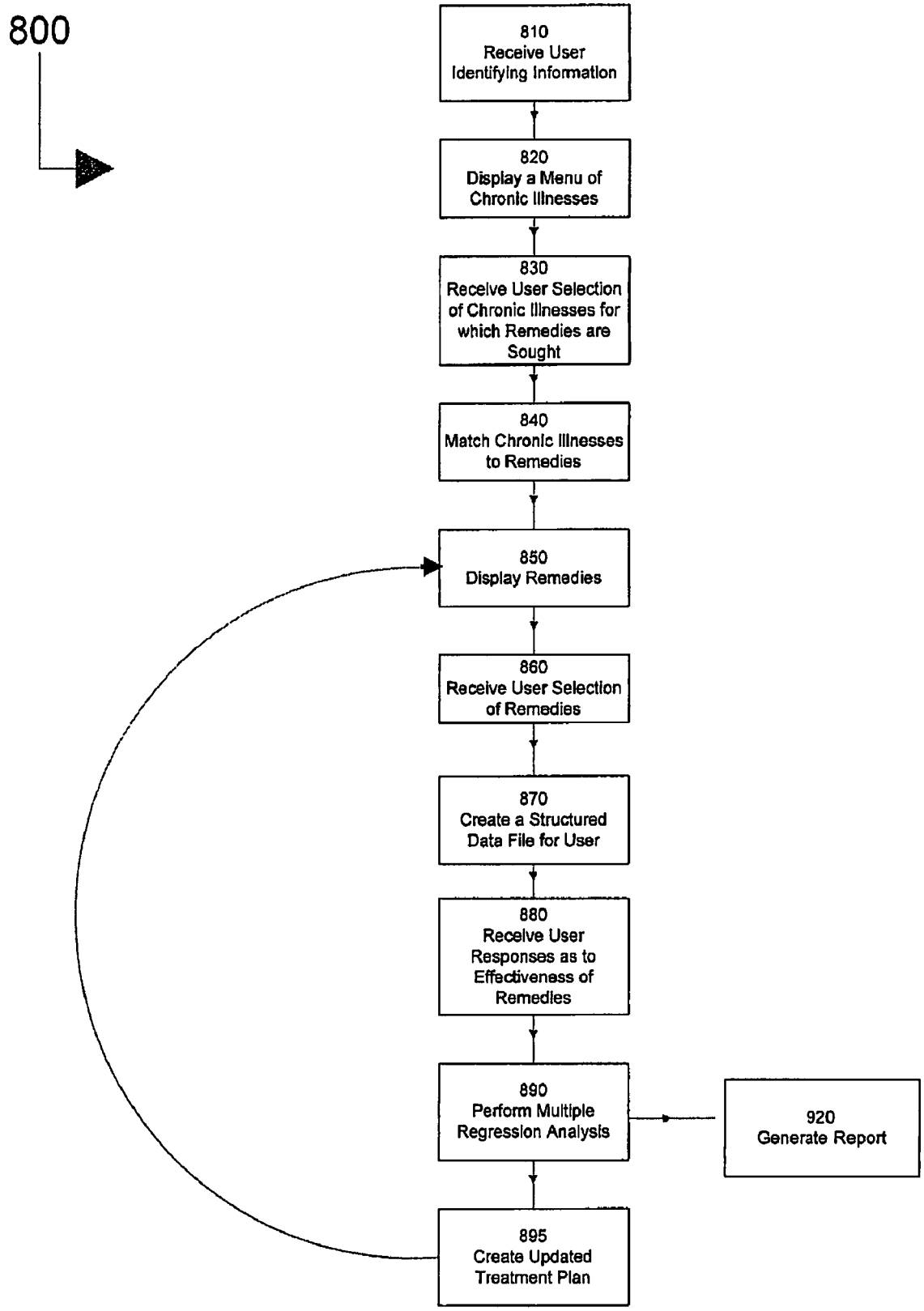
FIG. 9 is a flowchart of a method for creating an Individual Treatment Plan which generates reports.

FIG. 9 is a flowchart of Method 800 for creating an Individual Treatment Plan which further Step 920 for generating reports using a Report Generation Software Component. In the embodiment shown, reports generated include positive and negative responses, remedy interactions, patient progress, demographic data or any other data which the system described herein is capable of tracking.

Figure 10:
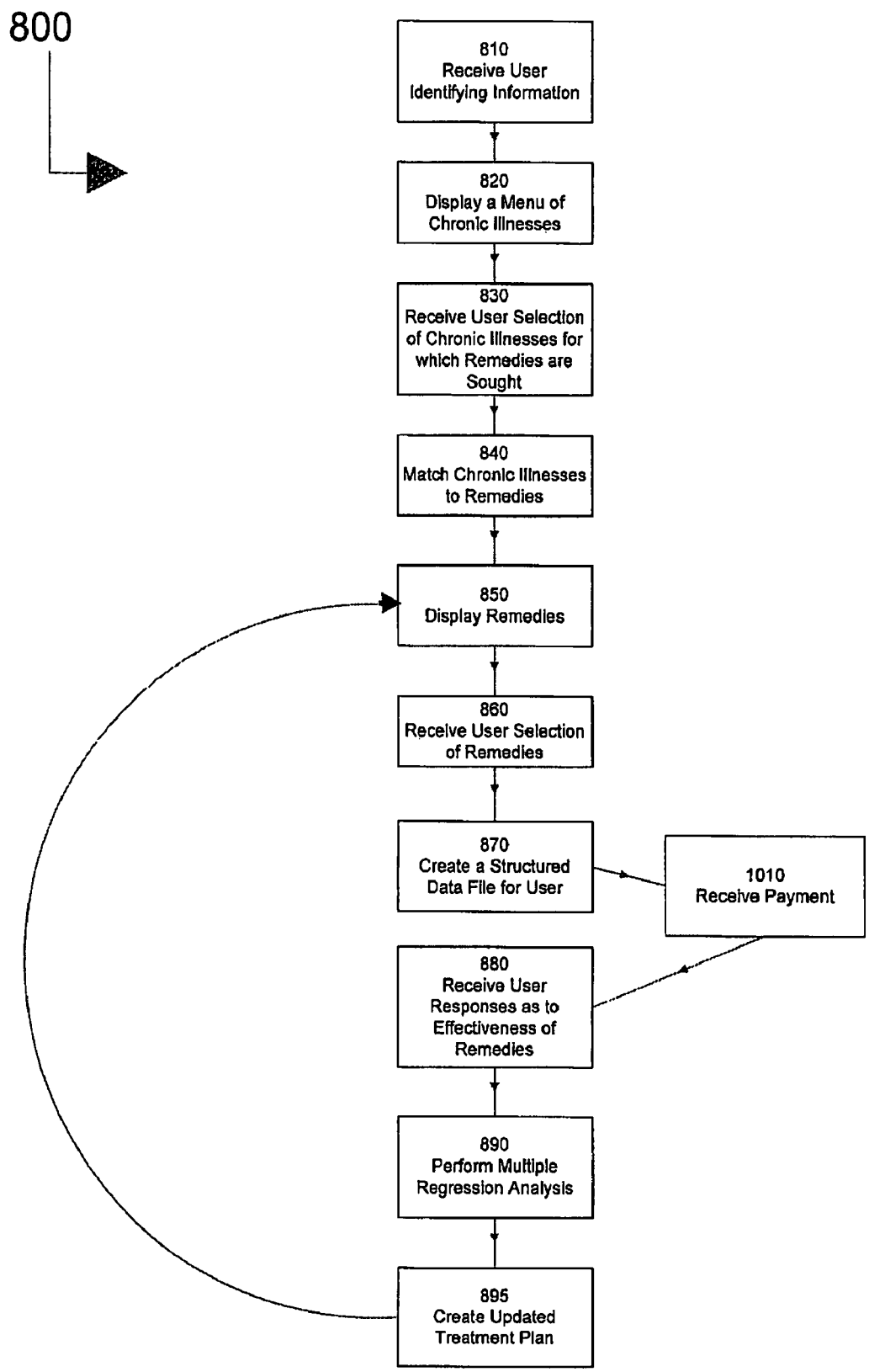
FIG. 10 is a flowchart of a method for creating an Individual Treatment Plan which receives payments.

FIG. 10 is a flowchart of Method 800 creating an Individual Treatment Plan which further includes Step 1010 for receiving payments. In the embodiment shown, a payment is required in order to save an Individual Treatment Plan for retrieval after in the future, but other embodiments may require no payment or may include additional steps for payment.

Figure 11:
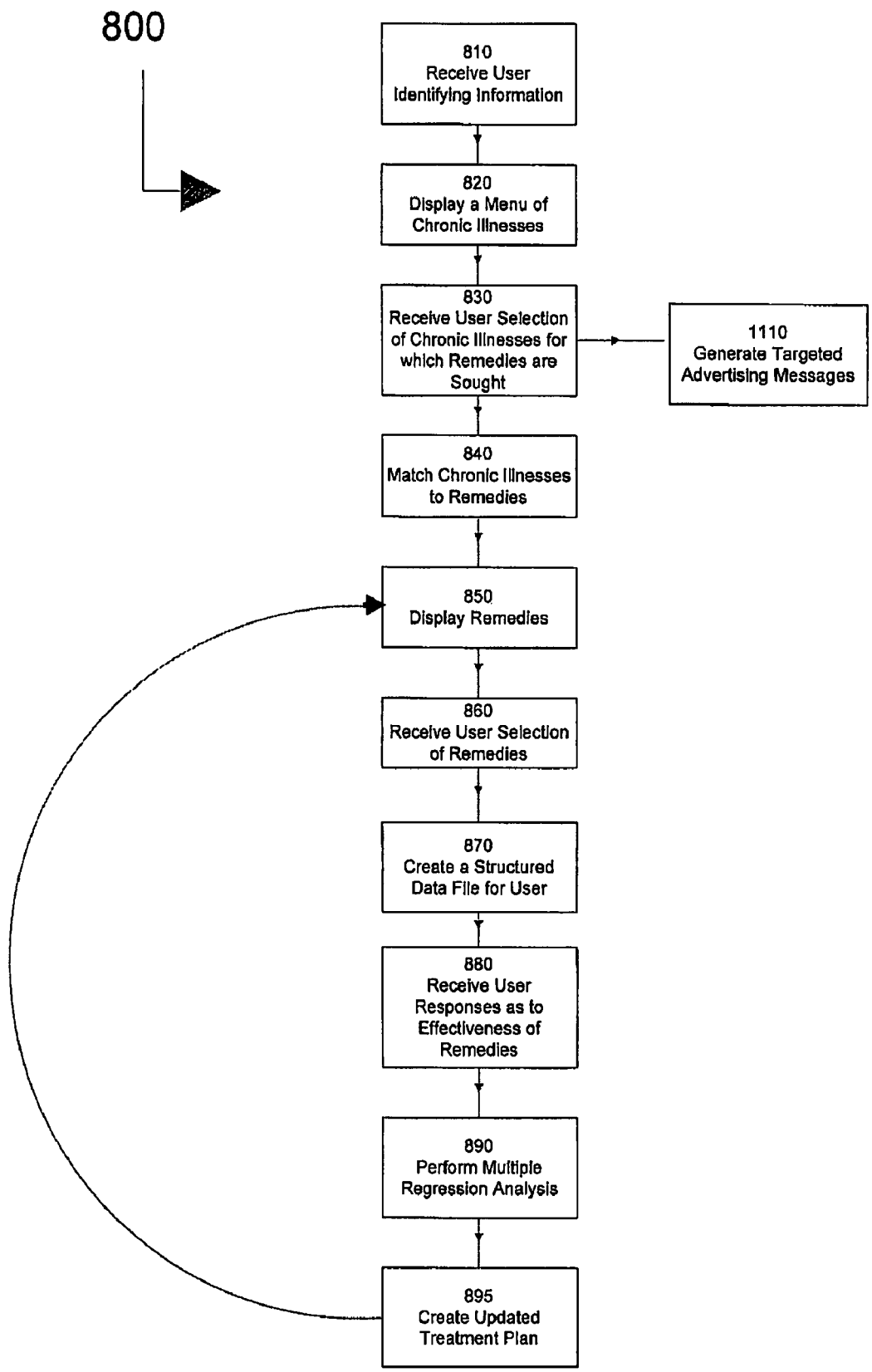
FIG. 11 is a flowchart of a method for creating an Individual Treatment Plan which generates Targeted Advertising Messages.

FIG. 11 is a flowchart of Method 800 for creating an Individual Treatment Plan which includes step 1110 for generating Targeted Advertising Messages. For example, in one embodiment, a user may input a specific chronic illness and receive one or more messages about new remedies, Health Care Professionals and/or support groups for persons suffering from that specific chronic illness.

Figure 12:
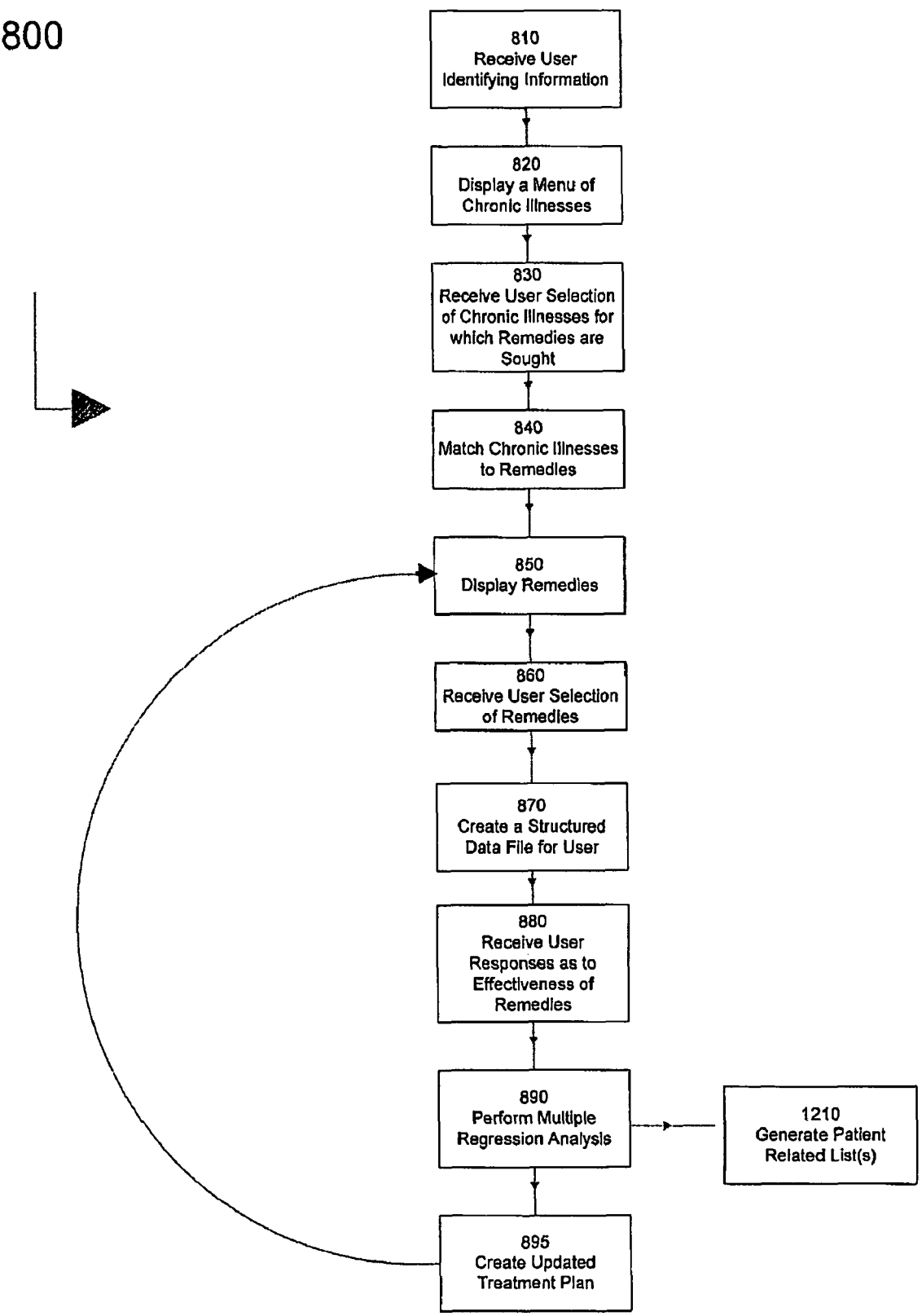
FIG. 12 is a flowchart of a method for creating an Individual Treatment Plan which generates patient-related lists.

FIG. 12 is a flowchart of a method for creating an Individual Treatment Plan which further includes Step 1210 for generating patient-related lists. In the embodiment shown, lists maybe created based on demographic data, geographical data, personal profile data, user responses, symptoms, any combination thereof, or any other data which the system described herein may be configured to track.

Figure 13:
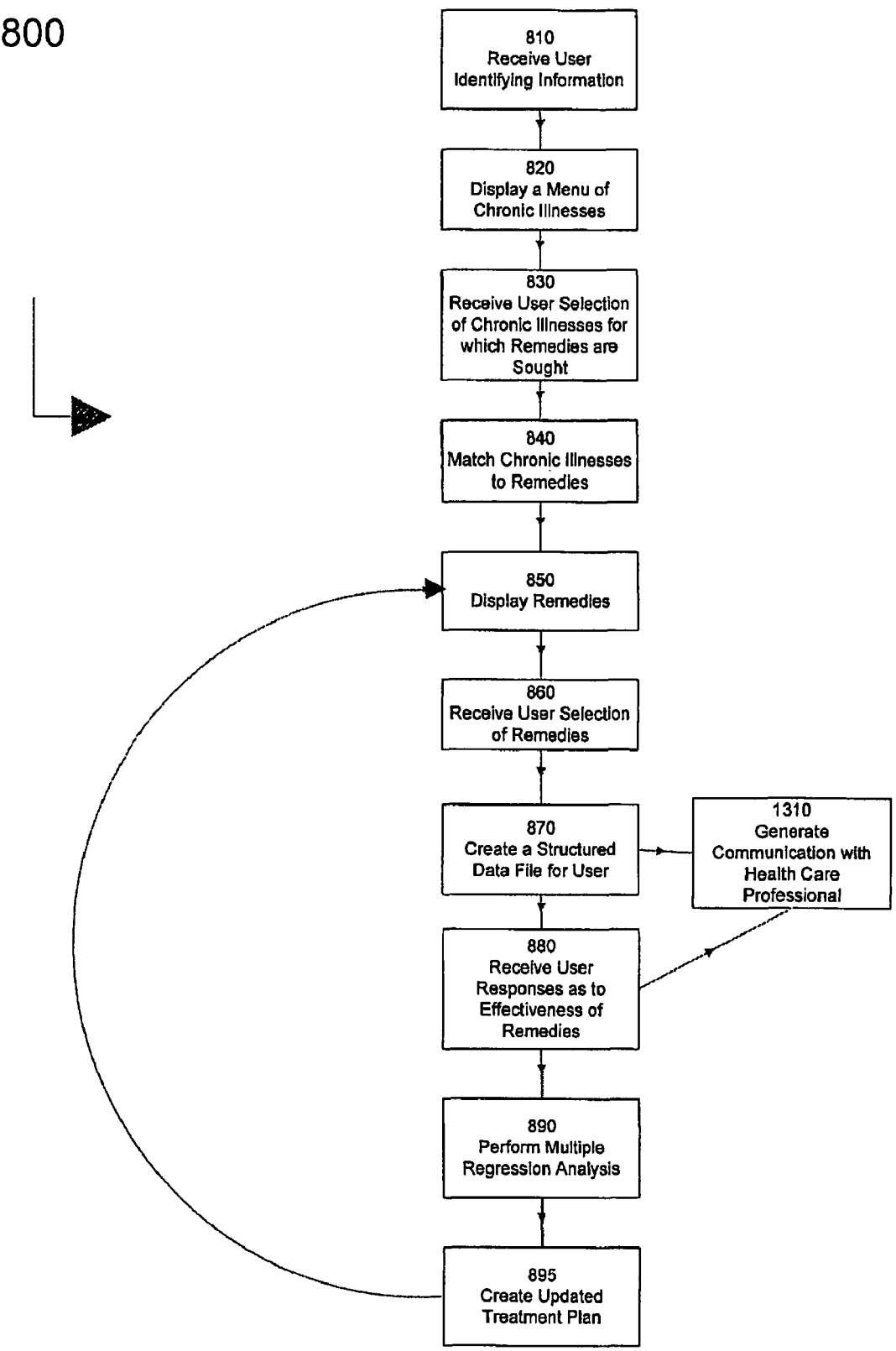
FIG. 13 is a flowchart of a method for creating an Individual Treatment Plan which enables Health Care Professionals to communicate with users.
Figure 14:
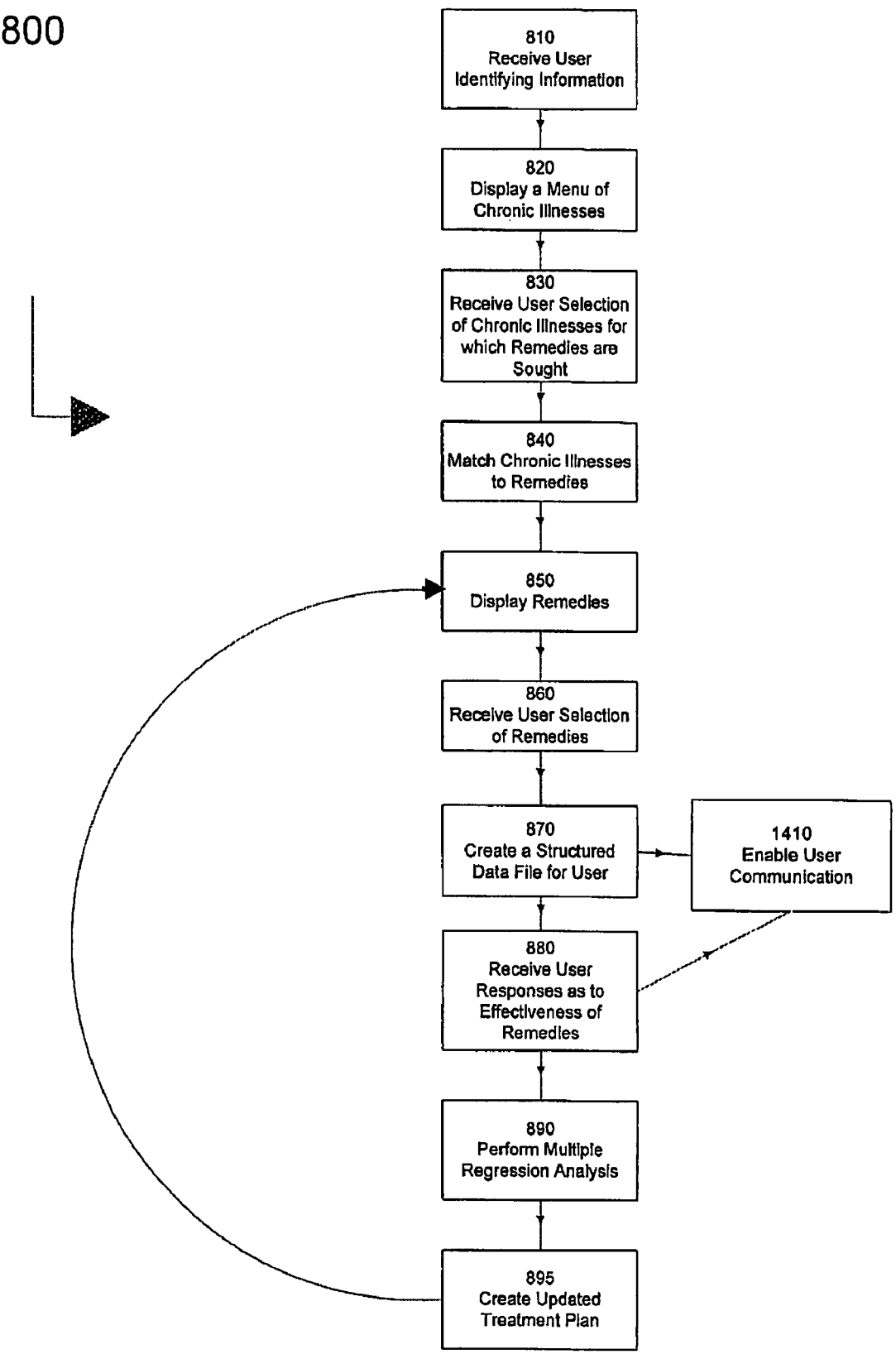
FIG. 14 is a flowchart of a method for creating an Individual Treatment Plan which enables users to communicate with each other.

FIG. 13 is a flowchart of a method for creating an Individual Treatment Plan which further includes Step 1310 for enabling Health Care Professionals to communicate with user This communication may be mandatory or discretionary, based on the configuration of the particular embodiment of the invention, and the communication may be in the form of an e-mail, facsimile, viewable interface, automated or non-automated phone call, pre-directed URL's, data pointers and software generated communication, FIG. 14 is a flowchart of a method for creating an Individual Treatment Plan which further includes which further includes Step 1410 for enabling Health Care Professionals to communicate with users. Social networking features may include blogs, list serves, group alerts, post-question formats, newsletter, personalized user pages or any other social networking feature known in the art.

Figure 15:
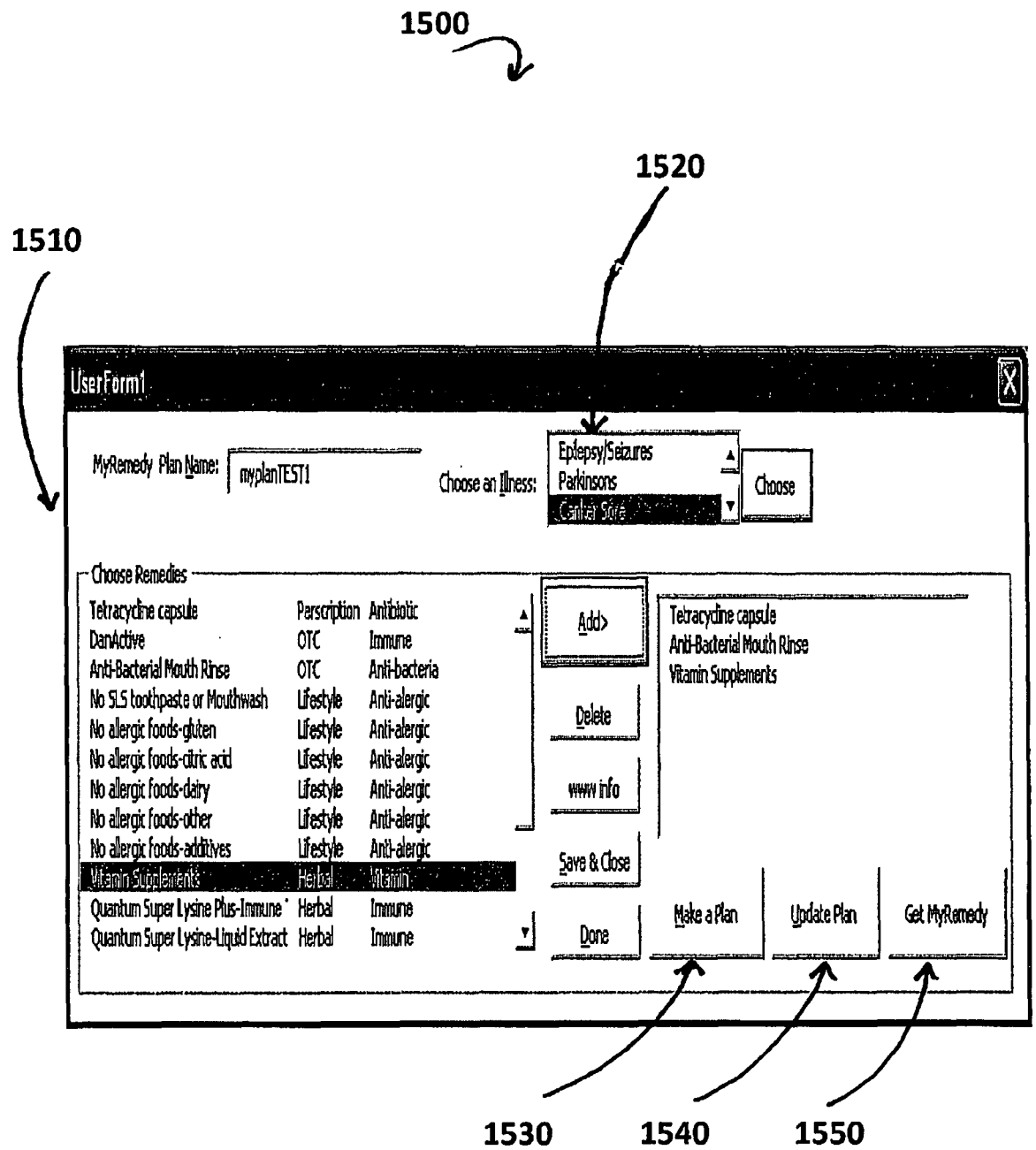
FIG. 15 is an exemplary embodiment of a user interface generated by the system and method described herein.

FIG. 15 is a sample embodiment of a Individual Treatment Plan displayed on user interfaces 1500 which includes menu of remedies 1510 and menu of chronic illnesses 1520. FIG. 15 further shows "Make Plan" activation button 1530 which invokes a Treatment Plan Software Component discussed supra. FIG. 15 also shows "Patient Update Software Component" activation button 1540 which invokes a Update Patient Software Component discussed supra. Finally, FIG. 15 shows "Get Remedy" activation button 1550 which invokes a Optimization Software Component discussed supra. Other embodiments may display fewer or more features, or may display them on a differently configured user interface, or may include other selection components such as radio buttons, drop-down lists, mouse-over activated features, touch screen features, voice data recognition features or any method of selection or activation known in the art.

What is claimed is:

1. A system for creating a treatment plan comprising:
   a server configured to display a user interface which includes a menu of chronic illnesses, said user interface further configured to communicate with a Relational Remedy Data Base and to display information received from said Relational Remedy Data bases;

said Relational Remedy Database Server of chronic illnesses and remedies configured to receive at least one menu-selected chronic illness from said user interface, to match said at least one menu-selected chronic illness to a plurality of remedies and to display said plurality of remedies on said user interface;

a Treatment Plan Software Component further configured to display a first updated user interface to enable a user to create an Individual Treatment Plan by selecting remedies from said plurality of remedies and to save said Individual Treatment Plan as a structured data file based on a Design of Treatment Process;

a Patient Data Update Software Component further configured to access said structured data file and further configured to receive additional input as to user selected remedies and receive responses from a user indicating said user's perceived effectiveness of said remedies; and an Optimization Software Component which performs a multiple regression analysis in which said user's response as to the perceived effectiveness of said remedies is used as an independent variable to determine an optimal subsequent combination of remedies based on said user responses, and which creates an Updated Treatment Plan, and which further communicates with said Patient Data Update Software Component to successively update and optimize said Updated Treatment Plan as desired.

2. The system of claim 1 wherein said Optimization Software Component is further configured to receive updated user-selected remedies and modify said multiple regression analysis based on said updated user-selected remedies.

3. The system of claim 1 which further includes a Report Generating Component which generates a Response Report selected from a group consisting of a report displayed on a user interface, a graph, a chart, a statistical analysis or an audio report.

4. The system of claim 1 which further includes a Payment Receiving Software Component for receiving payments to create said Individual Treatment Plan.

5. The system of claim 1 which further includes a Targeted Advertising Software Component which displays Targeted Advertising Information selected from a group consisting of a message relating to a user-selected chronic illness, a message relating to a remedy, an advertisement, a physician referral, a referral to a qualified health care professional, a support group referral, a related website, supplier information, care provider information, therapist information, health-related information, information about books, information about classes, information about charitable organizations, information about research facilities or any combination thereof.

6. The system of claim 1 which further includes a List Generating Software Component configured to create patient-related lists based on criteria selected from a group consisting of menu-selected chronic conditions, menu-selected remedies, patient response data, demographic information, geographical data, age data, race data, gender data or any combination thereof.

7. The system of claim 1 wherein said Relational Remedy Database Server is further configured to identify potential negative interactions among remedies.

8. The system of claim 1 wherein said Relational Remedy Database Server is further configured to identify potential negative interactions among remedies and perform an action selected from a group consisting of displaying a message, displaying updated interface to limit remedies displayed, allowing a user to elect remedies, dynamically creating an updated menu of remedies which may be selected by a user, displaying a warning message, activating an audible alarm, disabling user options or any combination thereof.

9. The system of claim 1 wherein said Relational Remedy Database Server may be modified by Health Care Professionals having permission to access the Relational Remedy Data Base.

10. The system of claim 1 which includes a Social Networking Software Component to facilitate social networking and communication between users having permission to access said Social Networking Software Component.

11. The system of claim 10 in which said Social Networking Software Component facilitates communication between patients and Health Care Professionals.

12. The system of claim 1 wherein said Relational Remedy Database Server may be modified by qualified health professionals having permission to access the Relational Remedy Data Base.

13. The system of claim 1 which further includes a Health Care Professional Communication Software Component for providing a Health Care Professional with a copy of a current treatment using a communication means selected from a group consisting of a facsimile, an e-mail, a document generated by the system, an access directing a physician to access an interface on which a treatment plan is displayed or any combination thereof.

14. A method comprising the steps of:
receiving identifying information from a user;
displaying a menu of chronic illnesses on a user interface;
receiving input from said user as to at least one selected chronic illness;
using a relational database server to match said at least one selected chronic illness to a plurality of remedies;
displaying said plurality of remedies on an updated user interface;
receiving user responses as to remedies selected;
creating a unique user structured data file including user identification data and said remedies selected using a Patient Update Software Component;
receiving user responses as to the effectiveness of remedies selected;
making said user responses as to the effectiveness of remedies selected an independent variable for use in a multiple regression analysis;
performing said multiple regression analysis using an Optimization Software Component to determine an optimal subsequent combination of remedies based on said user responses; and
creating an Updated Treatment Plan.

15. The method of claim 14 which further includes the step of receiving additional user-selected remedies and modifying said multiple regression analysis based on said additional user-selected remedies.

16. The method of claim 14 which further includes the step of creating a Response Report selected from a group consisting of a report displayed on a user interface, a graph, a chart, a statistical analysis or an audio report.

17. The method of claim 14 which further includes the step of receiving payments to create said Individual Treatment Plan.

18. The method of claim 14 which further includes the step of displaying Targeted Advertising Information selected from a group consisting of a message relating to a user-selected chronic illness, a message relating to a remedy, an advertisement, a physician referral, a referral to a qualified health care professional, a support group referral, a related website, supplier information, care provider information, therapist information, health-related information, information about books, information about classes, information about charitable organizations, or information about research.

19. The method of claim 14 which further includes the step of creating a patient-related list based on criteria selected from a group consisting of menu-selected chronic conditions, menu-selected remedies, patient response data, demographic information, geographical data, age data, race data, gender data or any combination thereof.

20. The method of claim 14 which further includes the step of identifying potential negative interactions among remedies and performing an action selected from a group consisting of displaying a message, displaying updated interface to limit remedies displayed, allowing a user to elect remedies, dynamically creating an updated menu of remedies which may be selected by a user, displaying a warning message, activate activating an audible alarm, disabling user options or any combination thereof.

21. The method of claim 14 which further includes the step of communicating with a Health Care Professional using a Social Networking Software Component to facilitate communication between a user and a Health Care Professional and generate a messages selected from a group consisting of a facsimile, an e-mail, a document generated by the system, an access directing a physician to access an interface on which a treatment plan is displayed or any combination thereof.

* * * * *